ANTI

(12) United States Patent
Faircloth et al.

(10) Patent No.: US 7,507,708 B2
(45) Date of Patent: Mar. 24, 2009

(54) ANTITUMORAL COMPOUNDS

(75) Inventors: Glynn Thomas Faircloth, Cambridge, MA (US); Maria del Carmen Cuevas Marchante, Madrid (ES)

(73) Assignee: Pharma Mar, S.A.U., Madrid (ES)

( * ) Notice: Subject to any disclaimer, the term of this patent is extended or adjusted under 35 U.S.C. 154(b) by 0 days.

(21) Appl. No.: 10/531,533

(22) PCT Filed: Oct. 20, 2003

(86) PCT No.: PCT/US03/33207

§ 371 (c)(1), (2), (4) Date: Apr. 25, 2006

(87) PCT Pub. No.: WO2004/035613

PCT Pub. Date: Apr. 29, 2004

(65) Prior Publication Data

US 2006/0234920 A1    Oct. 19, 2006

(30) Foreign Application Priority Data

Feb. 26, 2003  (GB) ................................. 0304367.6
Jun. 24, 2003  (GB) ................................. 0314725.3

(51) Int. Cl.
*A61K 38/00*    (2006.01)
*A61K 51/00*    (2006.01)

(52) U.S. Cl. ......................................... 514/2; 424/1.69
(58) Field of Classification Search ....................... 514/2
See application file for complete search history.

(56) References Cited

U.S. PATENT DOCUMENTS

| 4,670,261 | A | 6/1987 | Samejima et al. ........... 424/127 |
| 4,959,175 | A | 9/1990 | Yatzidis |
| 5,705,511 | A | 1/1998 | Hudkins et al. |
| 5,849,704 | A | 12/1998 | Sorensen et al. |
| 5,932,189 | A | 8/1999 | Dean et al. |
| 6,011,010 | A | 1/2000 | Gravalos et al. |
| 2003/0157685 | A1 | 8/2003 | Zervos |
| 2004/0052764 | A1 | 3/2004 | Hildinger et al. |
| 2004/0067895 | A1 | 4/2004 | Faircloth et al. |
| 2004/0214755 | A1 | 10/2004 | Albericio et al. |
| 2005/0054555 | A1 | 3/2005 | Jimeno et al. |

FOREIGN PATENT DOCUMENTS

| EP | 0 610 078 | 8/1994 |
| EP | 0 838 221 | 4/1998 |
| WO | WO 99/42125 | 8/1999 |
| WO | WO 01/58934 | 8/2001 |
| WO | WO 02/36145 | 5/2002 |
| WO | WO 03/033012 A1 | 4/2003 |
| WO | WO 2004/075910 | 9/2004 |
| WO | WO 2005/023846 | 3/2005 |
| WO | WO 2005/103072 | 11/2005 |

OTHER PUBLICATIONS

Vippagunta et al. Cystalline solids. Adv Drug Deliv Rev. May 16, 2001;48(1):3-26. Review.*
Guru. Cancer Models-Systems for identifying new drugs are often faulty. Science 278, 1041-2 (Nov. 7, 1997).*
U.S. Appl. No. 10/182,881, filed Jun. 3, 2003, Fernando Albericio et al.
U.S. Appl. No. 10/546,758, filed Aug. 24, 2005, Miguel Angel Izquierdo Delso.
U.S. Appl. No. 10/492,670, filed Nov. 3, 2004, Jose Jimeno.
U.S. Appl. No. 10/399,571, filed Nov. 14, 2003, Glynn Faircloth.
U.S. Appl. No. 10/642,006, filed Aug. 14, 2003, Paul Scheuer.
U.S. Appl. No. 10/570,734, filed Mar. 6, 2006, Fernando Albericio Palomera.
U.S. Appl. No. 11/587,177, filed Oct. 19, 2006, Andres Francesch Solloso.
G. M. Loudon, Organic Chemistry, Second Edition, Benjamin/Cummings Publishing Company, Inc., 1988, pp. 924-926.
Nuijen B et al., "Development of a lyophilized parenteral pharmaceutical formulation of the investigational polypeptide marine anticancer agent kahalalide F" Drug Development and Industrial Pharmacy, vol. 27, No. 8, pp. 767-780, 2001.
Faircloth G et al., "Preclinical development of kahalalide F, a new marine compound selected for clinical studies," Proceedings of the American Association for Cancer Research Annual, No. 41, Mar. 2000, pp. 600-601, XP001097542, 91st Annual Meeting of the American Association for Cancer Research, San Francisco CA, USA; Apr. 1-5, 2000, Mar. 2000 ISSN: 0197-016X.
Luber-Narod J et al., "Evaluation of the use of in vitro methodologies as tools for screening new compounds for potential in vivo toxicity." Toxicology In Vitro, vol. 15, No. 4-5, Aug. 2001, pp. 571-577, XP002225749, ISSN: 0887-2333, p. 576, col. 2, paragraph 2.
Brown Alan P et al., "Preclinical toxicity studies of kahalalide F, a new anticancer agent: single and multiple dosing regimens in the rat." Cancer Chemotherapy and Pharmacology. Germany Oct. 2002, vol. 50, No. 4, Oct. 2002, pp. 333-340, XP002225750 ISSN: 0344-5704 abstract.
El Sayed, Khalid A. et al., "The Marine Environment: A Resource for Prototype Antimalarial Agents," Journal of Natural Toxins, vol. 5, No. 2, pp. 261-285, 1996.
Garcia-Rocha, Mar et al., "The antitumoral compound Kahalalide F acts on cell lysosomes," Cancer Letters, vol. 99, No. 1, pp. 43-50, 1996.
Goetz, Gilles et al., "The Absolute Stereochemistry of Kahalalide F," Tetrahedron, vol. 55, pp. 7739-7746, 1999.
Goetz, Gilles et al., "Two Acyclic Kahalalides from the Sacoglossan Mollusk Elysia rufescens," Journal of Natural Products, vol. 60, No. 6, p. 562-567, 1997.
Hamann, Mark T. et al., "Kahalalide F: A Bioactive Depsipeptide from the Sacoglossan Mollusk Elysia refuscens and the Green Alga Bryopsis sp.," Journal of the American Chemical Society, vol. 115, No. 13, pp. 5825-5826, 1993.

(Continued)

*Primary Examiner*—Cecilia TSang
*Assistant Examiner*—Maury Audet
(74) *Attorney, Agent, or Firm*—Kenneth H. Sonnenfeld; Michael A. Willis; King & Spalding, LLP

(57) ABSTRACT

The present invention is directed to new kahalalide antitumoral compounds, in particular to analogues of kahalalide F, useful as antitumoral, antiviral, antifungal agents and in the treatment of psoriasis.

12 Claims, No Drawings

OTHER PUBLICATIONS

Hamann, Mark T. et al., "Kahalalides: Bioactive Peptides from a Marine Mollusk Elysia refuscens and Its Algal Diet Bryopsis sp.," The Journal of Organic Chemistry, vol. 61, No. 19, pp. 6594-6600, 1996.

Hamann, Mark T. et al., "Kahalalides: Bioactive Peptides from a Marine Mollusk Elysia refuscens and Its Algal Diet Bryopsis sp.," The Journal of Organic Chemistry, vol. 63, No. 14, pp. 4856, 1998.

Horgen, F. David et al., "A New Depsipeptide from the Sacoglossan Mollusk Elysia ornate and the Green Alga Bryopsis Species," Journal of Natural Products, vol. 63, No. 1, pp. 152-154, 2000.

Kan, Yukiko et al., "Kahalalide K: A New Cyclic Depsipeptide from the Hawaiian Green Algo Bryopsis Species," Journal of Natural Products, vol. 62, No. 8, pp. 1169-1172, 1999.

Lopez-Macia, Angel et al., "Kahalalide B. Synthesis of a natural cyclodepsipeptide," Tetrahedron Letters, vol. 41, pp. 9765-9769, 2000.

Goodman & Gilman's, The Pharmacological Basis of Therapeutics, Ninth Edition, McGraw Hill, New York (1996), Section X, Chemotherapy of Neoplastic Diseases, pp. 1225-1229.

Hamann, Mark Todd, Ph.D., University of Hawaii (1992), "Biologically Active Constituents of Some Marine Invertebrates," UMI Dissertation Services, published Oct. 1993.

Merck Manual, 11th ed., pp. 456-459, 761-763, and 1368-1371; published 1969.

Lee Y S et al., "A convergent liquid-phase synthesis of salmon calcitonin" Journal of Peptide Research, Munksgaard International Publishers, Copenhagen DK, vol. 54, No. 5, Oct. 1999, pp. 328-335, XP000849313 ISSN: 1397-002X, figure 1.

Bonnard Isabelle et al., "Stereochemistry of kahalalide F," Journal of Natural Products. Nov. 2003, vol. 66, No. 11, Nov. 2003, pp. 1466-1470, XP002337530 ISSN: 0163-3864 abstract.

Lopez-Macia et al., "Synthesis and Structure Determination of Kahalalide F." J. Am. Chem. Soc., vol. 123, No. 46, pp. 11398-11401, published on web Oct. 27, 2001.

GB Dermer, "Another Anniversary for the War on Cancer," Bio/Technology, Mar. 12, 1994, pp. 1-2.

"Cancer" [internet document] accessed Sep. 16, 2005, www.medterms.com, last reviewed Sep. 18, 2004, 1 page.

C. Gorman, et al., "The Hype and the Hope." Time, 1998, 151 (19), pp. 40-44, included HTML copy referenced pp. 1-9.

Freshney, Culture of Animal Cells, A Manual of Basic Technique, Alan R. Uss, Inc., 1983, New York., pp. 3-4.

R. McKie, "Cancer Research Set Back a Decade," The Observer, Jun. 10, 2001, pp. 1.-4.

Zips, et al., "New Anticancer Agents: In Vitro and In Vivo Evaluation," In Vivo, 2005, 19:1-7.

Angel Lopez i Macia, Ph.D. Thesis, Department de Quimica Organcia. Facultat de Quimica Divisio de Ciencies Experimentals i Matematiques, Universitat de Barcelona, catalogued Jan. 18, 2001.

Schellens et al., "Phase I and Pharmacokinetic Study of Kahalalide F in Patients with Advanced Androgen Resistant Prostate Cancer," American Society of Clinical Oncology, May 18-21, 2002, vol. 21, part 1 of 2, p. 113a.

Schellens et al., "Phase I and Pharmacokinetic Study of Kahalalide F in Patients with Advanced Androgen Refractory Prostate Cancer," AACR-NCI-EORTC International Conference, 2001.

Suggitt et al., "50 Years of Preclinical Anticancer Drug Screening: Empirical to Target-Driven Approaches," Clinical Cancer Research, vol. 11, Feb. 1, 2005, pp. 971-981.

English translation: Angel Lopez i Macia, Ph.D. Thesis, Department de Quimica Organica. Facultat de Quimica Divisio de Ciencies Experimentals i Matematiques, Universitat de Barcelona, catalogued Jan. 18, 2001, chapters 3, 4, and Conclusion.

* cited by examiner

ANTITUMORAL COMPOUNDS

FIELD OF THE INVENTION

The present invention is directed to new kahalalide antitumoral compounds, in particular to analogues of kahalalide F, where the aliphatic 5-methylhexanoic acid has been replaced by 4-methyl hexanoic acid, pharmaceutical compositions containing them and their use as antitumoral, antiviral, antifungal agents and in the treatment of psoriasis.

BACKGROUND OF THE INVENTION

The kahalalide compounds are peptides isolated from a Hawaiian herbivorous marine species of mollusc, *Elysia rufescens* and its diet, the green alga *Bryopsis*. sp. Kahalalides A-F are described in Hamman et al., J. Am. Chem. Soc., 1993, 115, 5825-5826.

Kahalalide A-G are described in Hamann, M. et al., J. Org. Chem, 1996, 61, 6594-6600: "Kahalalides: bioactive peptides from a marine mollusk *Elysia rufescens* and its algal diet *Bryopsis* sp.".

Kahalalide H and J are described in Scheuer P. J. et al., J. Nat. Prod. 1997, 60, 562-567: "Two acyclic kahalalides from the sacoglossan mollusk *Elysia rufescens*".

Kahalalide O is described in Scheuer P. J. et al., J. Nat. Prod. 2000, 63(1) 152-4: A new depsipeptide from the sacoglossan mollusk *Elysia ornata* and the green alga *Bryopsis* species".

For kahalalide K, see Kan, Y. et al., J. Nat. Prod. 1999 62(8) 1169-72: "Kahalalide K: A new cyclic depsipeptide from the hawaiian green alga *bryopsis* species".

For related reports, see also Goetz et al., Tetrahedron, 1999, 55; 7739-7746: "The absolute stereochemistry of Kahalalide F"; Albericio, F. et al. Tetrahedron Letters, 2000, 41, 9765-9769: "Kahalalide B. Synthesis of a natural cyclodepsipeptide"; Becerro et al. J. Chem. Ecol. 2001, 27(11), 2287-99: "Chemical defenses of the sarcoglossan mollusk *Elysia rufescens* and its host Alga *bryopsis* sp.".

Of the kahalalide compounds, kahalalide F is the most promising because of its antitumoral activity. Its structure is complex, comprising six amino acids as a cyclic part, and an exocyclic chain of seven amino acids with a terminal fatty acid group. Its activity against in vitro cell cultures of human lung carcinoma A-549 and human colon carcinoma HT-29 were reported in EP 610 078. Kahalalide F has also demonstrated to have antiviral and antifungal properties.

Preclinical in vivo studies determined that the maximum tolerated dose (MTD) of Kahalalide F in female mice following a single bolus iv injection was to be 280 µg/kg. Whereas single doses just above the MTDiv were extremely toxic, with animals exhibiting signs of neurotoxicity followed by death, 280 µg/kg Kahalalide F could be administered repeatedly, according to a once daily times five schedule, without any apparent evidence of acute toxicity. See Supko, F. et al., Proceedings of the 1999 AACR NCI EORTC International Conference, abstract 315: "Preclinical pharmacology studies with the marine natural product Kahalalide F".

WO 02 36145 describes pharmaceutical compositions containing kahalalide F and new uses of this compound in cancer therapy and is incorporated herein by reference in its entirety.

WO 03 33012, from which we claim priority, describes the clinical use in oncology of Kahalalide compounds and is incorporated herein by reference in its entirety.

GB 0304367, from which we also claim priority, describes the use of kahalalide compounds in the treatment of psoriasis and related ilnesses and is incorporated herein by reference in its entirety.

The synthesis and cytotoxic activities of natural and synthetic kahalalide compounds is described in WO 01 58934, which is incorporated herein by reference in its entirety. WO 01 58934 describes the synthesis of Kahalalide F and also of compounds with a similar structure in which the terminal fatty acid chain is replaced by other fatty acids.

There is still a need to provide further antitumoral compounds, in particular further Kahalalide compounds with improved properties.

SUMMARY OF THE INVENTION

We have unexpectedly found that one of the kahalalide analogue compounds shows promising activity and improved antitumoral efficacy in in vivo models.

The present invention is directed to a compound of formula 1:

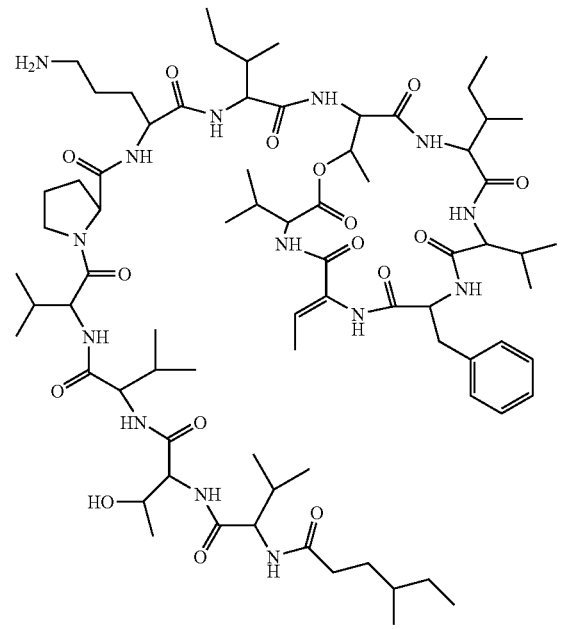

Formula 1 and to pharmaceutically acceptable salts, prodrugs, tautomers, and solvates, thereof.

This compound corresponds to Kahalalide F with a 4-methylhexanoic terminal fatty acid chain, and will be referred to hereinafter as 4-methylhexanoic KF.

In a preferred embodiment the invention is directed to the compound containing (4S)-methyl hexanoic acid, having the chemical name: 4(S)-MeHex-D-Val-L-Thr-L-Val-D-Val-D-Pro-L-Orn-D-allo-Ile-cyclo(D-allo-Thr-D-allo-Ile-D-Val-L-Phe-Z-Dhb-L-Val) and to pharmaceutically acceptable salts, prodrugs, tautomers, and solvates, thereof. This compound will be referred to hereinafter as (4S)-methyihexanoic KF.

The present invention is also directed to a pharmaceutical composition comprising a compound as previously defined and a pharmaceutically acceptable carrier, vehicle or diluent.

The present invention further provides a method of treating any mammal, notably a human, affected by cancer or psoriasis which comprises administering to the affected individual a therapeutically effective amount of a compound as defined above.

The present invention can be employed particularly for treatment of patients with refractory cancers that do not respond favourably to other treatments. In particular, the compositions of this invention can be employed after other chemotherapy has been tried and not worked.

The present invention is particularly directed to the treatment of patients affected with prostate cancer, breast cancer, hepatocellular carcinoma, melanoma, colorectal cancer, renal cancer, ovarian cancer, NSCL cancer, epithelial cancer, pancreatic cancer and tumors that overexpress the Her2/neu oncogene.

In another aspect the present invention is directed to the use of a compound as defined above in the manufacture of a medicament. In a preferred embodiment the medicament is for the treatment of cancer, psoriasis, viral infection or fungal infection.

The invention additionally provides kits comprising separate containers containing a pharmaceutical composition comprising a compound as defined above and a reconstituting agent. Methods of reconstitution are also provided.

The invention is also directed to a process for the preparation of a compound as defined above. Preferably the process uses 4-methylhexanoic acid as starting material. In a preferred embodiment the 4-methylhexanoic acid is (4S)-methylhexanoic acid. In a most preferred embodiment the process is a solid phase synthesis.

DETAILED DESCRIPTION OF THE INVENTION

We have identified analogues of Kahalalide F that show significant improvement in activity with respect to Kahalalide F. As shown in the comparative examples, the 4-methylhexanoic KF has unexpectedly shown significant improved efficacy in in vivo cancer models. This is the more surprising in view of the small structural difference between 4-methylhexanoic KF and 5-methylhexanoic KF.

The compound of the invention is Kahalalide F with a 4-methylhexanoic fatty acid chain instead of 5-methylhexanoic, and has a structure according to formula 1:

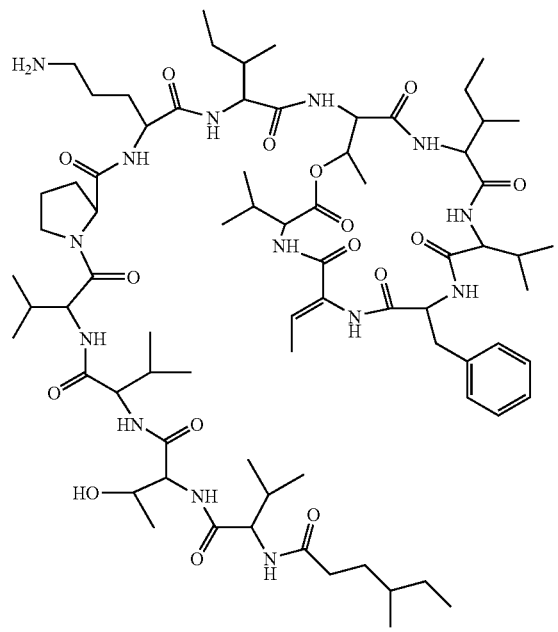

In particular we prefer that the compound has a stereochemistry as defined by the chemical name: 4(S)-MeHex-D-Val-L-Thr-L-Val-D-Val-D-Pro-L-Orn-D-allo-Ile-cyclo (D-allo-Thr-D-allo-Ile-D-Val-L-Phe-Z-Dhb-L-Val).

Nevertheless the compounds of the present invention have asymmetric centers and therefore exist in different enantiomeric and diastereomic forms. This invention relates to the use of all optical isomers and stereoisomers of the compounds of the present invention, and mixtures thereof, and to all pharmaceutical compositions and methods of treatment that may employ or contain them.

For convenience, we refer to the compounds of this invention, notably compounds 1 and 2, as 4-methylhexyl kahalide F compounds, or 4-mehexKF compounds. Preferably the 4-mehexKF compounds of this invention are largely free, substantially free or completely free of other kahalalide compounds. For example, the 4-mehexKF of this invention is preferably free of kahalalide F having a 5-methylhexyl sidechain. In particular, the 4-mehexKF of this invention preferably contains at most 25%, 10%, 5%, 2%, 1% or 0.5%, or less than 0.5% of any other kahalalide, notably kahalalide F. In a related aspect, the 4-mehexKF of this invention is provided in a substantially pure form. Such a 4-mehexKF compound free to some extent of other kahalalides is especially suited for pharmaceutical compositions and treatment methods of this invention.

The present invention includes the compounds of the present invention, and the pharmaceutically acceptable salts thereof, wherein one or more hydrogen, carbon or other atoms are replaced by isotopes thereof. Such compounds may be useful as research and diagnostic tools in metabolism pharmacokinetic studies and in binding assays.

As used herein, the compounds of this invention, including the compounds of formula 1 and 2, are defined to include pharmaceutically acceptable derivatives or prodrugs thereof. A "pharmaceutically acceptable derivative or prodrug" means any pharmaceutically acceptable salt, ester, salt of an ester or other derivative of a compound of this invention that, upon administration to a recipient, is capable of providing (directly or indirectly) a compound of this invention or a metabolite or residue thereof. Particularly favored derivatives and prodrugs are those that increase the bioavailability of the compounds of this invention when such compounds are administered to a patient (e.g., by allowing an orally administered compound to be more readily absorbed into the blood), enhance delivery of the parent compound to a given biological compartment, increase solubility to allow administration by injection, alter metabolism or alter rate of excretion.

Salts of the compounds of the present invention may comprise acid addition salts derived from a nitrogen in the compound of formula 1 or 2. The therapeutic activity resides in the moiety derived from the compound of the invention as defined herein and the identity of the other component is of less importance although for therapeutic and prophylactic purposes it is, preferably, pharmaceutically acceptable to the patient. Examples of pharmaceutically acceptable acid addition salts include those derived from mineral acids, such as hydrochloric, hydrobromic, phosphoric, metaphosphoric, nitric and sulphuric acids, and organic acids, such as tartaric, acetic, trifluoroacetic, citric, malic, lactic, fumaric, benzoic, glycolic, gluconic, succinic and methanesulphonic and arylsulphonic, for example p-toluenesulphonic, acids. A preferred salt is the trifluoro acetic salt.

The compounds of the present invention can be prepared according to the synthetic process described in WO 01 58934, for example adding the appropriate (S) or (R) 4-methylhexanoic acid instead of 5-methylhexanoic in example 3 of WO 01 58934. Therefore also encompassed by the invention is a process to prepare a compound according to formula 1 or 2. Preferably the process uses 4-methylhexanoic acid as starting material. Most preferably the starting material is (4S)-methylhexanoic acid. The synthesis is preferably a solid phase synthetic process. Furhter detail on the synthesis is given in the examples.

The process of this invention can be carried out from starting materials in an enantio-, stereocontrolled and fast manner, taking advantages of the solid-phase synthetic methodology, where the molecule in construction is bounded to an insoluble support during all synthetic operations.

Pharmaceutical formulations of the compounds of the invention may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier (s) or excipient (s).

Preferably pharmaceutical compositions of the compounds of the invention include liquid (solutions, suspensions or emulsions) with suitable composition for intravenous administration, and they may contain the pure compound or in combination with any carrier or other pharmacologically active compounds. Further guidance concerning the pharmaceutical compositions can be found in WO 02 36145 which is incorporated herein by reference in its entirety.

Thus, a combination of a non-ionic surfactant and an organic acid is suited for use with a bulking agent to give a lyophilised form of a compound of the invention suited for reconstitution. Reconstitution is preferably effected with a mix of emulsifying solubiliser, alkanol and water.

The lyophilised composition preferably comprises mainly the bulking agent, such as at least 90% or at least 95% bulking agent. Examples of bulking agents are well known and include sucrose and mannitol. Other bulking agents can be employed.

The non-ionic surfactant in the lyophilised composition is preferably a sorbitan ester, more preferably a polyethylene sorbitan ester, such as a polyoxyethylene sorbitan alkanoate, especially a polyoxyethylene sorbitan mono-oleate, for example polysorbate 80. The non-ionic surfactant typically comprises a few % of the composition, such as 0 to 5% of the composition, for instance 2 to 3 or 4% of the composition.

The organic acid in the lyophilised composition is typically an aliphatic acid, preferably a hydroxycarboxylic acid and more preferably a hydroxypolycarboxylic acid, notably citric acid. The organic acid typically comprises a few % of the composition, such as 0 to 5% of the composition, for instance 2 to 3 or 4% of the composition.

The amount of the compound of the invention in the lyophilised composition is typically less than 1%, or often less than 0.1%, of the mix. A suitable amount is in the range 50 to 200 μg, say about 100 μg, per 100 mg of composition.

The emulsifying solubiliser for the reconstituting agent suitably comprises an polyethylene glycol ester, notably an ester of a fatty acid, more preferably a PEG oleate such as PEG-35 oleate. The emulsifying solubiliser is suitably 0 to 10% of the reconstituting agent, typically about 3 to 7%, say about 5%. The alkanol is usually ethanol, and is suitably 0 to 10% of the reconstituting agent, typically about 3 to 7%, say about 5%. The remainder of the reconstituting agent is water, and gives a reconstituted solution suited for intravenous injection.

Further dilution of the reconstituted solution with 0.9% saline may be appropriate for infusion of the kahalalide compound. Suitable infusion equipment preferably includes a glass container, rather than one of polyethylene. Tubing is preferably of silicone.

The preferred reconstituting agent then comprises 2 to 7%, say about 5%, emulsifying solubiliser; 2 to 7%, say about 5%, alcohol; and remainder water.

The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use.

Thus the invention additionally provides kits comprising separate containers containing the lyophilised composition and the reconstituting agent. Methods of reconstitution are also provided.

Administration of the compounds or compositions of the present invention is by intravenous infusion. Infusion times of up to 72 hours can be used, more preferably 1 to 24 hours, with either about 1 or about 3 hours most preferred. Short infusion times which allow treatment to be carried out without an overnight stay in hospital are especially desirable. However, infusion may be around 24 hours or even longer if required.

The administration is performed in cycles, in the preferred application method, an intravenous infusion of a compound of the invention is given to the patients the first week of each cycle, the patients are allowed to recover for the remainder of the cycle. The preferred duration of each cycle is of either 1, 3 or 4 weeks; multiple cycles can be given as needed. In an alternative dosing protocol, the compound of the invention is administered for say about 1 hour for 5 consecuvitve days every 3 weeks. Other protocols can be devised as variations.

Dose delays and/or dose reductions and schedule adjustments are performed as needed depending on individual patient tolerance of treatments, in particular dose reductions are recommended for patients with higher than normal serum levels of liver transaminases or alkaline phosphatase.

In one aspect, the present invention provides a method for treating a human patient afflicted with cancer, comprising administering to said patient a compound of the invention at a dose below 1200 mcg/m2/day, preferably below 930 mcg/m2/day and more preferably below 800 mcg/m2/day. Suitably the dose is at least 320 mcg/m2/day. Preferably the dose is in the range of 400-900 mcg/m2/day, preferably 500-800 mcg/m2/day, more preferably 600-750 mcg/m2/day. Especially preferred are doses of about 650-700 mcg/m2/day.

In a further aspect the invention provides a method for treating a human patient afflicted with cancer, comprising administering to said patient a compound of the invention daily during 5 days at a dose below 930 mcg/m2/day, followed by a resting period of from 1 to 4 weeks in which the kahalalide compound is not administered. The dose is preferably 650-750 mcg/m2/day, more preferably about 700 mcg/m2/day. The infusion time is preferably between 1 and 24 hours, more preferably between 1 and 3 hours. Especially preferred is an infusion time of about 1 or about 3 hours. The resting period is preferably 2-3 weeks, more preferably about 2 weeks.

The present invention also provides a method for treating a human patient afflicted with cancer, comprising administering to said patient a compound of the invention once weekly at a dose below 800 mcg/m2/day. The dose is preferably 600-700 mcg/m2/day, more preferable 650 mcg/m2/day. The infusion time is preferably between 1 and 24 hours, more preferably between 1 and 3 hours. Especially preferred is an infusion time of about 1 hour.

Although guidance for the dosage is given above, the correct dosage of the compound will vary according to the particular formulation, the mode of application, and the particular situs, host and tumour being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

The present invention is particularly directed to the treatment of patients affected with prostate cancer, breast cancer, hepatocellular carcinoma, melanoma, colorectal cancer, renal cancer, ovarian cancer, NSCL cancer, epithelial cancer, pancreatic cancer and tumors that overexpress the Her2/neu oncogene. Most preferably it is directed to the treatment of hepatocellular cancer, melanoma, breast and prostate cancer.

The present invention is also directed to a method of treating a skin disease involving hyperproliferation of dermis cells in a mammal which comprises administering to the mammal an effective, non-toxic amount of a compound of the invention. The skin disease is preferably psoriasis. The present invention is preferably directed to the treatment of human patients affected with psoriasis, in particular severe psoriasis.

The compounds and compositions of this invention may be used with other drugs to provide a combination therapy. The other drugs may form part of the same composition, or be provided as a separate composition for administration at the same time or a different time. The identity of the other drug is not particularly limited, although combination with other chemotherapeutic, hormonal or antibody agents is envisaged. The amounts of the compound of the invention and the other pharmaceutically active agent or agents and the relative timings of administration will be selected in order to achieve the desired combined therapeutic effect.

EXAMPLES

Example 1

Preparation of (4S)-methylhexanoic KF

General Procedures and the initial steps of the process are as described in WO 01 58934.

(4S)-MeHex-D-Val-Thr(tBu)-Val-D-Val-D-Pro-Orn (Boc)-D-allo-Ile-D-allo-Thr (Val-Alloc)-D-allo-Ile-D-Val-O-TrtCl-resin The Fmoc group was removed and Fmoc-Val-OH (678 mg, 2 mmol, 4 equiv), Fmoc-Thr(tBu)-OH (992 mg, 2.5 mmol, 5 equiv), Fmoc-D-Val-OH (678 mg, 2 mmol, 4 equiv), and (4S)-MeHex-OH (195 mg, 1.5 mmol, 3 equiv) were sequentially added to the above peptidyl-resin (Example 3) using DIPCDI (233 µL, for 1.5 mmol and 3 equiv; 310 µL, for 2 mmol and 4 equiv; and 388 µL, for 2.5 mmol, 5 equiv) and HOBt (230 mg, for 1.5 mmol and 3 equiv; 307 mg, for 2 mmol and 4 equiv; and 395 mg, 2.5 mmol. 5 equiv) for 90 min. In all cases, after 90 min of coupling, the ninhydrin test was negative. Removal of Fmoc group and washings were carried out as described in General Procedures.

(4S)-MeHex-D-Val-Thr(tBu)-Val-D-Val-D-Pro-Orn (Boc)-D-allo-Ile-D-allo-Thr (Val-Z-Dhb-Phe-Alloc)-D-allo-Ile-D-Val-O-TrtCl-resin Alloc group was removed with $Pd(PPh_3)_4$ (58 mg, 0.05 mmol, 0.1 equiv) in the presence of $PhSiH_3$ (617 µL, 5 mmol, 10 equiv) under atmosphere of Ar and Alloc-Phe-Z-Dhb-OH (666 mg, 2 mmol, 4 equiv) and HOAt (273 mg, 2 mmol, 4 equiv) were dissolved in DMF (1.25 mL) and added to peptidyl-resin, then DIPCDI (310 µL, 2 mmol, 4 equiv) was added and the mixture stirred for 5 h, where the ninhydrin test was negative. After washings with DMF and $CH_2Cl_2$, an aliquot of the peptidyl-resin was treated with TFA-$H_2O$ (1:99) for 1 min and the product was characterized by MALDI-TOF-MS, calcd for $C_{88}H_{146}N_{14}O_{21}$, 1,736.18. Found: m/z 1,758.67 [M+Na]$^+$, 1,774.62 1,618.2 [M+K]$^+$.

(4S)-MeHex-D-Val-Thr(tBu)-Val-D-Val-D-Pro-Orn (Boc)-D-allo-Ile-D-allo-Thr (Val-Z-Dhb-Phe-H)-D-allo-Ile-D-Val-OH After washings with DMF and $CH_2Cl_2$, the Alloc group was removed with $Pd(PPh_3)_4$ (58 mg, 0.05 mmol, 0.1 equiv) in the presence of $PhSiH_3$ (617 µL, 5 mmol, 10 equiv) under atmosphere of Ar. The protected peptide was cleaved from the resin by TFA-$CH_2Cl_2$ (1:99) (5×30 sec). Filtrate were collected on $H_2O$ (4 mL) and the $H_2O$ was partially removed in a rotavapor. ACN was then added to dissolve solid that appeared during the $H_2O$ removal, and the solution was lyophilized, to give 639 mg (387 µmol, 77% yield) of the title compound with a purity of >95% as checked by HPLC (Condition A, $t_R$ 10.5 min).

(4S)-MeHex-D-Val-Thr-Val-D-Val-D-Pro-Orn-D-allo-Ile-cyclo(D-allo-Thr-D-allo-Ile-D-Val-Phe-Z-Dhb-Val)=(4S)methylhexanoic KF The protected peptide (Example 6) (639 mg, 387 µmol) was dissolved in $CH_2Cl_2$ (390 mL, 1 mM), and HOBt (237 mg, 1.55 mmol) dissolved in the minimum volume of DMF to dissolve HOBt, DIEA (203 µL, 1.16 mmol, 3 equiv), and DIPCDI (240 µL, 1.55 mmol, 4 equiv) were added. The mixture was allowed to stir for 1 h, then the course of the cyclization step was checked by HPLC. The solvent was removed by evaporation under reduced pressure. The protected cyclic peptide was dissolved in TFA-$H_2O$ (19:1, 85 mL) and the mixture was allowed to stir for 1 h. The solvent was removed by evaporation under reduced pressure, and dioxane is added (30 mL) and the solvent is removed by evaporation under reduced pressure (the process was repeated three times), then $H_2O$ (40 mL) was added and lyophilized. The crude product was purified by HPLC (Kromasil $C_8$ 5 µm, 205×50 mm), isocratic 44% acetonitrile (+0.05% TFA) in water (+0.05% TFA), 55 mL/h, detection at 220 nm, to give the title product (192 mg, 0.13 mmol, 26% yield, 92.3%). MALDI-TOF-MS, calcd for $C_{75}H_{124}N_{14}O_{16}$, 1,477.9. Found: m/z 1,500.12 [M+Na]$^+$, 1,515.97 [M+K]$^+$. The $^1$H-NMR (2.5 mM; 500 MHz, $H_2O$-$D_2O$ (9:1) spectrum of the compound is indicated in Table I).

TABLE I

| RESIDUE | N—H | Hα | Hβ | OTHER |
|---|---|---|---|---|
| (Z)-Dhb | 9.59(s) | — | 6.63(q, J=7.5Hz) | 1.19(d, γ-$CH_3$) |
| D-al•lo-Ile 1 | 8.82(d, J=9.0Hz) | 4.42 | 1.87 | 1.25, 1.09, 0.82(γ-$CH_2$, γ-$CH_3$, δ-$CH_3$) |
| L-Phe | 8.75(d, J=5.5Hz) | 4.63 | 3.08(m) | 7.31(2H Ar, t) 7.25(3H Ar, d) |
| D-al•lo-Thr | 8.67(d, J=9.0Hz) | 4.64 | 5.05(m) | 1.21(γ-$CH_3$) |
| D-Val 3 | 8.13(d, J=7.5Hz) | 4.33 | 2.01 | 0.90(2γ-$CH_3$) |
| L-Orn | 8.29(d, J=7.5Hz) | 4.31 | 1.66(2H) | 1.88(γ-$CH_2$), 2.96(bs, δ-$CH_2$), 7.56(ε-$NH_3^+$) |
| D-al•lo-Ile 2 | 7.92(d) | 4.18 | 1.80 | 1.25, 1.09, 0.81(γ-$CH_2$, γ-$CH_3$, δ-$CH_3$) |
| D-Val 5 | 8.01(d) | 4.08 | 2.07 | 0.87(2γ-$CH_3$) |
| L-Thr | 8.19(d, J=7.5Hz) | 4.29 | 4.14(m) | 1.13(γ-$CH_3$) |
| D-Val 2 | 7.89(d, J=7.5Hz) | 4.32 | 2.11 | 0.78(γ-$CH_3$) |
| L-Val 4 | 8.04(d) | 4.10 | 2.07 | 0.90(2γ-$CH_3$) |
| L-Val 1 | 7.19(d, J=9Hz) | 4.02 | 1.52 | 0.75(γ-$CH_3$), 0.65(d, γ-$CH_3$) |
| D-Pro | — | 4.36 | 2.23, 1.99(m, β-$CH_2$) | 1.85(m, γ-$CH_2$), 3.83(1H, m, δ-$CH_2$), 3.64(1H, m, δ-$CH_2$) |
| 4(S)-MeHex | — | 2.26 (2H) | 1.57(b-$CH_2$), 1.26, 1.10, 1.33, 0.79(d-$CH_2$, δ-$CH_3$, γ-CH, ε-$CH_3$) | |

$^1$H-NMR spectroscopy [1H, NOESY, TOCSY at (278K)] was performed on a Varian Unity Plus (500 MHz). Chemical shifts (d) are expressed in parts per million downfield from TMS. Coupling constants are expressed in hertz.

Example 2

Preparation of (4R)-methylhexanoic KF

Experimental procedures as decribed in Example 1, starting with 1 g of resin, were carried out with the only exceptions that, in the appropriate step, (4S)-MexHex was replaced by (4R)-MexHex. The product (220 mg, 0.15 mmol, 30%, 92.3% purity) was characterized by ES-MS, $C_{75}H_{124}N_{14}O_{16}$, 1,477.9. Found: m/z 1,499.07 [M+Na]$^+$, 1,514.94 [M+K]$^+$.

Example 3

In Vitro Cytotoxic Activity

The finality of these assays is to interrupt the growth of a "in vitro" tumor cell culture by means a continued exhibition of the cells to the sample to be testing.

Cell Lines

| Name | N° ATCC | Species | Tissue | Characteristics |
|---|---|---|---|---|
| P-388 | CCL-46 | mouse | ascites fluid | lymphoid neoplasm |
| K-562 | CCL-243 | human | leukemia | erythroleukemia (pleural effusion) |
| A-549 | CCL-185 | human | lung | lung carcinoma "NSCL" |
| SK-MEL-28 | HTB-72 | human | melanoma | malignant melanoma |
| HT-29 | HTB-38 | human | colon | colon adenocarcinoma |
| LoVo | CCL-229 | human | colon | colon adenocarcinoma |
| LoVo-Dox | | human | colon | colon adenocarcinoma (MDR) |
| SW620 | CCL-228 | human | colon | colon adenocarcinoma (lymph node metastasis) |
| DU-145 | HTB-81 | human | prostate | prostate carcinoma, not androgen receptors |
| LNCaP | CRL-1740 | human | prostate | prostate adenocarcinoma, with androgen receptors |
| SK-BR-3 | HTB-30 | human | breast | breast adenocarcinoma, Her2/neu+, (pleural effusion) |
| MCF-7 | HTB-22 | human | breast | breast adenocarcinoma, (pleural effusion) |
| MDA-MB-231 | HTB-26 | human | breast | breast adenocarcinoma, Her2/neu+, (pleural effusion) |
| IGROV-1 | | human | ovary | ovary adenocarcinoma |

-continued

| Name | N° ATCC | Species | Tissue | Characteristics |
|---|---|---|---|---|
| IGROV-ET | | human | ovary | ovary adenocarcinoma, characterized as ET-743 resistant cells |
| SK-OV-3 | HTB-77 | human | ovary | ovary adenocarcinoma (malignant ascites) |
| OVCAR-3 | HTB-161 | human | ovary | ovary adenocarcinoma |
| HeLa | CCL-2 | human | cervix | cervix epitheloid carcinoma |
| HeLa-APL | CCL-3 | human | cervix | cervix epitheloid carcinoma, characterized as aplidine resistant cells |
| A-498 | HTB-44 | human | kidney | kidney carcinoma |
| PANC-1 | CRL-1469 | human | pancreas | pancreatic epitheloid carcinoma |
| HMEC1 | | human | endothelium | |

A colorimetric type of assay, using sulforhodamine B (SRB) reaction has been adapted for a quantitative measurement of cell growth and viability [following the technique described by Philip Skehan, et al. (1990), New colorimetric cytotoxicity assay for anticancer drug screening, *J. Natl. Cancer Inst.*, 82:1107-1112]

This form of the assay employs 96 well cell culture microplates of 9 mm diameter (Faircloth, 1988; Mosmann, 1983). Most of the cell lines are obtained from American Type Culture Collection (ATCC) derived from different human cancer types.

Cells are maintained in RPMI 1640 10% FBS, supplemented with 0.1 g/l penicillin and 0.1 g/l streptomycin sulfate and then incubated at 37° C., 5% $CO_2$ and 98% humidity. For the experiments, cells were harvested from subconfluent cultures using trypsin and resuspended in fresh medium before plating.

Cells are seeded in 96 well microtiter plates, at $5 \times 10^3$ cells per well in aliquots of 195 μl medium, and they are allowed to attach to the plate surface by growing in drug free medium for 18 hours. Afterward, samples are added in aliquots of 5 μl in a ranging from 10 to $10^{-8}$ μg/ml, dissolved in DMSO/EtOH/PBS (0.5:0.5:99). After 48 hours exposure, the antitumor effect are measured by the SRB methodology: cells are fixed by adding 50 μl of cold 50% (wt/vol) trichloroacetic acid (TCA) and incubating for 60 minutes at 4° C. Plates are washed with deionized water and dried. One hundred μl of SRB solution (0.4% wt/vol in 1% acetic acid) is added to each microtiter well and incubated for 10 minutes at room temperature. Unbound SRB is removed by washing with 1% acetic acid. Plates are air dried and bound stain is solubilized with Tris buffer. Optical densities are read on a automated spectrophotometric plate reader at a single wavelength of 490 nm.

The values for mean +/− SD of data from triplicate wells are calculated. Some parameters for cellular responses can be calculated: GI=growth inhibition, TGI=total growth inhibition (cytostatic effect) and LC=cell killing (cytotoxic effect).

Results are given in table II, there is no significant difference between the compounds:

TABLE II

Activity Data (Molar).

| CELL LINE | | 5-methhex•KF | (4S)-methhex KF | (4R)-methhex KF |
|---|---|---|---|---|
| DU-145 | GI50 | 7.51E-07 | 2.37E-07 | 1.20E-06 |
| | TGI | 1.64E-06 | 6.97E-07 | 2.14E-06 |
| | LC50 | 3.60E-06 | 2.49E-06 | 3.82E-06 |
| LN-caP | GI50 | 9.61E-07 | 1.12E-06 | 1.50E-06 |
| | TGI | 2.31E-06 | 2.58E-06 | 2.46E-06 |
| | LC50 | 5.57E-06 | 5.93E-06 | 4.04E-06 |
| SKOV-3 | GI50 | — | — | — |
| | TGI | — | — | — |
| | LC50 | — | — | — |
| IGROV | GI50 | 4.20E-07 | 2.92E-07 | 9.41E-07 |
| | TGI | 1.40E-06 | 7.51E-07 | 1.81E-06 |
| | LC50 | 3.80E-06 | 2.62E-06 | 3.50E-06 |
| IGROV-ET | GI50 | 4.47E-07 | 2.25E-07 | 8.05E-07 |
| | TGI | 9.54E-07 | 4.79E-07 | 1.62E-06 |
| | LC50 | 3.09E-06 | 2.82E-06 | 3.26E-06 |
| SK-BR-3 | GI50 | 3.98E-07 | 1.81E-07 | 1.25E-06 |
| | TGI | 4.48E-06 | 3.32E-06 | 2.20E-06 |
| | LC50 | 6.77E-06 | 6.06E-07 | 3.86E-06 |
| MEL-28 | GI50 | 6.90E-07 | 1.43E-06 | 1.14E-06 |
| | TGI | 1.56E-06 | 2.60E-06 | 2.09E-06 |
| | LC50 | 3.55E-06 | 4.72E-06 | 3.80E-06 |
| H-MEC-1 | GI50 | — | — | — |
| | TGI | — | — | — |
| | LC50 | — | — | — |
| A-549 | GI50 | 8.66E-07 | 2.67E-07 | 1.20E-06 |
| | TGI | 1.81E-06 | 7.17E-07 | 2.26E-06 |
| | LC50 | 3.78E-06 | 3.09E-06 | 4.24E-06 |
| K-562 | GI50 | 1.54E-06 | 2.52E-06 | 3.73E-06 |
| | TGI | 2.95E-06 | 6.77E-06 | 6.77E-06 |
| | LC50 | 5.66E-06 | 6.77E-06 | 6.77E-06 |
| PANC-1 | GI50 | 1.38E-06 | 6.77E-06 | 4.70E-06 |
| | TGI | 2.89E-06 | 6.77E-06 | 4.24E-06 |
| | LC50 | 6.07E-06 | 6.77E-06 | 4.24E-06 |
| HT-29 | GI50 | 1.41E-06 | 3.01E-07 | 7.38E-07 |
| | TGI | 2.81E-06 | 7.51E-07 | 1.54E-06 |
| | LC50 | 5.62E-07 | 2.71E-06 | 3.22E-06 |
| LOVO | GI50 | 1.20E-07 | 1.63E-07 | 2.48E-07 |
| | TGI | 2.26E-07 | 3.08E-07 | 7.78E-07 |
| | LC50 | 4.28E-07 | 5.80E-07 | 2.28E-06 |
| LOVO-DOX | GI50 | 1.62E-07 | 1.57E-07 | 2.88E-07 |
| | TGI | 3.17E-07 | 3.25E-07 | 7.71E-07 |
| | LC50 | 6.20E-07 | 6.77E-07 | 2.19E-06 |
| HELA | GI50 | 8.39E-07 | 1.18E-06 | 1.05E-06 |
| | TGI | 1.89E-06 | 2.42E-06 | 1.93E-06 |
| | LC50 | 4.26E-06 | 4.97E-06 | 3.55E-06 |
| HELA-APL | GI50 | 1.06E-06 | 1.04E-06 | 1.56E-06 |
| | TGI | 2.17E-06 | 2.13E-06 | 3.47E-06 |
| | LC50 | 4.43E-06 | 4.39E-06 | 6.77E-06 |

Example 4

In vitro Toxicity

In order to assess the cytotoxicity of the drugs to normal cells, we used 96 well plates plated at a density of 5000 cells per well with normal cell lines maintained as per the directions of the ATCC: AML-12, normal mouse liver cells and NRK-52E, normal rat kidney cell. The cells in each plate were permitted to settle overnight before adding the test drug. To each well (100 µl medium) 10 µl of drug in media was added at varying concentrations ($1 \times 10^{-10}$-0.01 mg/ml final concentration) and further incubated overnight at 37° C. with 5% $CO_2$. All experiments were repeated at least 3 times and were assayed in duplicate. After 24 h the MTS assay (CellTiter 96 aqueous) was performed according to the manufacturer's (Promega) directions (for all cell types). Cell viability (mitochondrial activity) is determined via enzymatic conversion of the formazan substrate.

As can be seen from the results in Table III, there is no significant difference between the compounds 5 methylhexanoic KF and (4S)-methylhexanoic KF.

TABLE III

|  | ALM Liver $IC_{50}$ (µM) | NRK Kidney $IC_{50}$ (µM) |
| --- | --- | --- |
| 5-methylhexanoic KF | 3.4 | 2.7 |
| (4S)-methylhexanoic KF | 5.4 | 2.7 |

Example 5

In vivo MTD in CD-1 Mice and in Athymic Animals

The Maximum Tolerated Dose is determined in CD-1 and athymic mice (both genders) for each drug after single bolus administration and after 5 dayly doses. The results are given in table IV, there is no significant difference between the compounds 5 methylhexanoic KF and (4S)-methylhexanoic KF.

TABLE IV

|  | 5-methylhexanoic KF | (4S)-methylhexanoic KF |
| --- | --- | --- |
| Male CD-1 mice MTD Bolus | 300 | 300 |
| Female CD-1 mice MTD Bolus | 200 | 200 |
| Male CD-1 mice MTD 5DD | 175-350 | 175-350 |
| Female CD-1 mice MTD 5DD | 175-350 | 175-350 |
| Male athymic mice MTD Bolus | 350 | 350 |
| Female athymic mice MTD Bolus | 325 | 325 |
| Male athymic mice MTD 5DD | 350 | 350 |
| Female athymic mice MTD 5DD | 325 | 325 |

Example 6

In vivo Efficacy in Breast Xenografts (5DD)

The efficacy of 5-methylhexanoic KF and (4S)-methylhexanoic KF each at the three quarters maximum tolerated dose (MTD) level, was analyzed in breast xenografts following an administration regimen of five consecutive daily (i.e., QD×5) intravenous (iv) bolus injections (Days 0-4) in female athymic mice. The compounds were provided as freshly prepared vialed solutions in vehicle [Cremophor-EL/Ethanol/Water (5:5:90)]. Each daily dose (of QD×5 schedule) was administered iv in an injection volume of 0.2 ml per 20 gram animal.

Evaluation of net tumor growth of the corresponding treated group relative to the vehicle control group (i.e., % ΔT/ΔC) indicated that the lowest (optimal) value occurred on Day 3 after initiation of drug treatment for all groups. In addition, pair-wise statistical analyses (using the Mann-Whitney, non-parametric method) revealed that, unexpectedly in view of their very similar structure and in view of the previous examples, there was a significant difference in efficacy between the two compounds.

Based on efficacy studies described herein and toxicity experiments performed earlier (example 4) a therapeutic index of at least 1.33 (1×MTD/0.75×MTD, dose at which drug is toxic/dose at which drug is efficacious) can be assigned to (4S)-methylhexanoic KF. In addition, a biologically relevant observation was that the antitumor effect of (4S)-methylhexanoic KF in breast was longer lasting than in prostate xenografts (example 7), at the same relative MTD dose. In summary, (4S)-methylhexanoic KF clearly appears to be the more potent isomer in breast xenografts and the duration of its biological action suggests that it has a long lasting impact in this type of tumor.

TABLE V

|  | Dose µg/kg | Net tumor Growth $mm^3$, n = 9 | % ΔT/ΔC |
| --- | --- | --- | --- |
| Control | — | 167 | 100 |
| 5-methylhexanoic KF | 245 | 108 | 65 |
| (4S)-methylhexanoic KF | 245 | 74 | 44 |

Example 7

In vivo Efficacy in Prostate Xenografts (5DD)

The efficacy of 5-methylhexanoic KF and (4S)-methylhexanoic KF at one dose each, was analyzed in prostate xenografts following an administration regimen of five consecutive daily (i.e., QD×5) intravenous (iv) bolus injections (Days 0-4) in male athymic mice. The compounds were provided as freshly prepared vialed solutions in vehicle [Cremophor-EL/Ethanol/Water (5:5:90)]. Each daily dose (of QD×5 schedule) was administered iv in an injection volume of 0.2 ml per 20 gram animal.

Evaluation of net tumor growth of the corresponding treated group relative to the vehicle control group (i.e., % ΔT/ΔC) indicated that the lowest (optimal) value occurred on Day 3 after initiation of drug treatment for all groups. In addition, pair-wise statistical analyses (using a Mann-Whitney, non-parametric method) revealed that significantly more efficacy was achieved with (4S)-methylhexanoic KF at a 262 µg/kg/day dose. Base on efficacy studies described herein and toxicity experiments performed earlier (example 4), a therapeutic index of at least 1.33 (1×MTD/0.75×MTD, dose at which drug is toxic/dose at which drug is efficacious) can be assigned to (4S)-methylhexanoic KF. The results are listed in Table VI below.

TABLE VI

| | Dose (µg/kg) | Net tumor Growth mm$^3$, n = 10 | % ΔT/ΔC |
|---|---|---|---|
| Control | — | 236 | 100 |
| 5-methylhexanoic KF | 262 | 126 | 53 |
| (4S)-methylhexanoic KF | 262 | 62 | 26 |

Example 8

Antitumor Activity of Kahalalide F Analogs in Hollow Fiber Using a Panel of Human Tumor Cell Lines The antitumor activity of the Kahalalide F analogs discussed above has been tested in the hollow fiber (HF) system using a panel of human tumor cell lines, namely, SK-Hep-1 (hepatoma), HepG2 (hepatocellular carcinoma), Panc-1 (pancreas), and Mel-28 (melanoma). The human tumor cells are encapsulated in HFs in vitro and later implanted into female athymic mice in vivo.

Doses of 5 methylhexanoic KF and (4S)-methylhexanoic KF were selected on the basis of prior MTD experiments carried out in athymic mice resulting in a dosage of 325 µg/kg/day (see example 5). Five consecutive daily doses were administered intraperitoneal (ip) in an injection volume of 0.2 ml per 20 gram animal.

Overall, KF-4(S)-Met demonstrates statistically significant antitumor activity against hepatoma (sc), hepatocellular carcinoma (both ip and sc), pancreas (ip), and shows a trend towards significance (i.e., P=0.059) in the sc compartment in pancreas and melanoma. In contrast, KF-5-Met is active in fewer tumor types, namely, only pancreas (both ip and sc), and melanoma (sc), but not any type of the liver cancers tested. A summary of the results is listed on the table below, which clearly show the differences between the compounds.

| | TUMOR TYPE/HF LOCATION (arbitrary number of cells/HF) | | | | | | | |
|---|---|---|---|---|---|---|---|---|
| | SK-Hep-1 | | HepG2 | | Panc-1 | | Mel-28 | |
| DRUG | ip | sc | ip | sc | ip | sc | ip | sc |
| Vehicle | 0.575 | 0.872 | 0.576 | 0.509 | 0.200 | 0.392 | 2.078 | 1.77 |
| KF-4(S)-Met | 0.485 | 0.525* | 0.335* | 0.319* | 0.129* | 0.237§ | 1.906 | 1.51 |
| KF-5-Met | 0.693 | 0.686 | 0.475 | 0.361 | 0.149* | 0.192* | 1.771 | 1.56 |

*Statistically significant, P < 0.05.
§Trend towards significance, i.e., P = 0.059.

The invention claimed is:

1. A purified compound of formula 1:

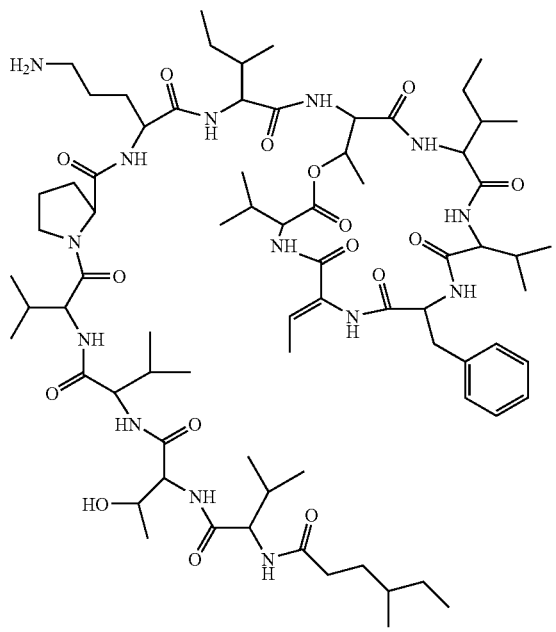

Formula 1 and pharmaceutically acceptable salts thereof.

2. A compound according to claim 1, wherein the compound is 4(S)-MeHex-D-Val-L-Thr-L-Val-D-Val-D-Pro-L-Orn-D-allo-Ile-cyclo(D-allo-Thr-D-allo-Ile-D-Val-L-Phe-Z-Dhb-L-Val), and pharmaceutically acceptable salts thereof.

3. A pharmaceutical composition comprising a purified compound according to any one of claim 1 or 2 and a pharmaceutically acceptable carrier, vehicle or diluent.

4. A kit comprising separate containers containing a pharmaceutical composition comprising a compound according to any one of claim 1 or 2 and a reconstituting agent.

5. A method of preparing a compound according to any one of claim 1 or 2 comprising:
converting 4-MeHex-D-Val-L-Thr(tBu)-L-Val-D-Val-D-Pro-L-Orn(Boc)-D-allo-Ile-D-allo-Thr(L-Val-Z-Dhb-L-Phe-H)-D-allo-Ile-D-Val-OH
to 4-MeHex-D-Val-L-Thr-L-Val-D-Val-D-Pro-L-Orn-D-allo-Ile-cyclo(D-allo-Thr-D-allo-Ile-D-Val-L-Phe-Z-Dhb-L-Val).

6. A method for preparing a compound according to claim 1 comprising:
providing 4-methyl hexanoic acid as a starting material in a process for preparing the compound according to claim 1.

7. A method for preparing a compound according to claim 2 comprising:
providing (4S)-methyl hexanoic acid as a starting material in a process for preparing the compound according to claim 2.

8. A method of treating a mammal having cancer comprising:
administering to the mammal a therapeutically effective amount of a compound according to any one of claim 1 or 2 wherein the form of cancer is selected from the group consisting of prostate, ovarian, breast, melanoma, lung, leukemia, pancreatic, colon, cervical and hepatic.

9. The method according to claim 8, wherein the mammal is a human.

10. The method according to claim 8, wherein the cancer is a refractory cancer.

11. The method according to claim 8, wherein the form of cancer is selected from melanoma, colon, ovarian, lung, leukemia, and pancreatic.

12. The method according to claim 8, wherein the cancer is selected from hepatocellular carcinoma, human liver adenocarcinoma, breast cancer, and prostate cancer.

* * * * *